US009889154B2

(12) United States Patent
Basadonna et al.

(10) Patent No.: US 9,889,154 B2
(45) Date of Patent: *Feb. 13, 2018

(54) HEMOSTATIC COMPOSITIONS, DEVICES, AND METHODS (71) Applicant: Z-MEDICA, LLC, Wallingford, CT (US)

(72) Inventors: Giacomo Basadonna, Haddam, CT (US); Brent A. Johnson, Ladera Ranch, CA (US)

(73) Assignee: Z-MEDICA, LLC, Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/995,592

(22) Filed: Jan. 14, 2016

(65) Prior Publication Data

US 2016/0120901 A1     May 5, 2016

Related U.S. Application Data (63) Continuation of application No. 14/479,214, filed on Sep. 5, 2014, which is a continuation of application No. 13/240,795, filed on Sep. 22, 2011, now Pat. No. 8,858,969.

(60) Provisional application No. 61/385,388, filed on Sep. 22, 2010.

(51) Int. Cl.
| | |
|---|---|
| A61K 9/70 | (2006.01) |
| A61K 33/06 | (2006.01) |
| A61F 13/00 | (2006.01) |
| A61F 13/36 | (2006.01) |
| A61K 8/02 | (2006.01) |
| A61K 9/14 | (2006.01) |
| A61L 15/28 | (2006.01) |
| A61L 15/44 | (2006.01) |
| A61L 15/60 | (2006.01) |
| A61L 26/00 | (2006.01) |
| A61M 11/00 | (2006.01) |
| A61M 35/00 | (2006.01) |

(52) U.S. Cl.
CPC ........ *A61K 33/06* (2013.01); *A61F 13/00034* (2013.01); *A61F 13/00063* (2013.01); *A61F 13/36* (2013.01); *A61K 8/0208* (2013.01); *A61K 9/14* (2013.01); *A61L 15/28* (2013.01); *A61L 15/44* (2013.01); *A61L 15/60* (2013.01); *A61L 26/0004* (2013.01); *A61L 26/0066* (2013.01); *A61L 26/0076* (2013.01); *A61M 11/007* (2014.02); *A61M 35/003* (2013.01); *A61F 2013/00472* (2013.01); *A61L 2300/404* (2013.01); *A61L 2400/04* (2013.01); *A61M 2202/064* (2013.01)

(58) Field of Classification Search
None
See application file for complete search history.

(56) References Cited

U.S. PATENT DOCUMENTS

| | | |
|---|---|---|
| 2,688,586 A | 9/1954 | Eberl et al. |
| 2,969,145 A | 1/1961 | Hannuer, Jr. |
| 3,122,140 A | 2/1964 | Crowe et al. |
| 3,181,231 A | 5/1965 | Breck |
| 3,189,227 A | 6/1965 | Hobbs et al. |
| 3,366,578 A | 1/1968 | Michalko |
| 3,386,802 A | 6/1968 | Michalko |
| 3,538,508 A | 11/1970 | Young |
| 3,550,593 A | 12/1970 | Kaufman |
| 3,608,070 A | 9/1971 | Nouvel |
| 3,658,984 A | 4/1972 | Kamp |
| 3,698,392 A | 10/1972 | Vogt et al. |
| 3,723,352 A | 3/1973 | Warner et al. |
| 3,763,900 A | 10/1973 | Solms-Baruth et al. |
| 3,979,335 A | 9/1976 | Golovko et al. |
| 4,373,519 A | 2/1983 | Errede et al. |
| 4,374,044 A | 2/1983 | Schaefer et al. |
| 4,379,143 A | 4/1983 | Sherry et al. |
| 4,435,512 A | 3/1984 | Ito et al. |
| 4,460,642 A | 7/1984 | Errede et al. |
| 4,514,510 A | 4/1985 | Alexander |
| 4,524,064 A | 6/1985 | Nambu |
| 4,525,410 A | 6/1985 | Hagiwara et al. |
| 4,569,343 A | 2/1986 | Kimura et al. |
| 4,626,550 A | 12/1986 | Hertzenberg |
| 4,631,845 A | 12/1986 | Samuel et al. |
| 4,651,725 A | 3/1987 | Kifune et al. |

(Continued)

FOREIGN PATENT DOCUMENTS

| | | |
|---|---|---|
| CA | 1 223 208 | 6/1987 |
| CN | 101104080 | 1/2008 |

(Continued)

OTHER PUBLICATIONS

"Mastering the Art of Innovative Thinking," (color brochure) FMC BioPolymer, 2001 FMC Corporation.

Alam, et al., Application of a Zeolite Hemostatic Agent Achieves 100% Survival in a Lethal Model of Complex Groin Injury in Swine, May 2004, The Journal of Trauma Injury, Infection, and Critical Care, vol. 56, pp. 974-983.

Alam, et al., Comparative Analysis of Hemostatic Agents in a Swine Model of Lethal Groin Injury, Jun. 2003, The Journal of Trauma Injury, Infection, and Critical Care, vol. 54, No. 6, pp. 1077-1082.

Aldrich—Handbook of Fine Chemicals and Laboratory Equipment, 2000-2001, pp. 1177-1178.

(Continued)

*Primary Examiner* — Susan Tran
(74) *Attorney, Agent, or Firm* — Knobbe, Martens, Olson & Bear, LLP (57) ABSTRACT

Compositions that include a clay such as kaolin dispersed in a liquid such as water may be useful for promoting the clotting of blood. The compositions may be in a liquid, gel, paste, foam, or another form. Uses may include treating a traumatic injury such as in injury caused by a bullet, an explosive, a blade etc., or an injury caused during a medical procedure such as surgery.

12 Claims, 4 Drawing Sheets

(56) References Cited

U.S. PATENT DOCUMENTS

| | | |
|---|---|---|
| 4,717,735 A | 1/1988 | Stem |
| 4,728,323 A | 3/1988 | Matson |
| 4,748,978 A | 6/1988 | Kamp |
| 4,822,349 A | 4/1989 | Hursey et al. |
| 4,828,081 A | 5/1989 | Nordstrom et al. |
| 4,828,832 A | 5/1989 | DeCuellar et al. |
| 4,911,898 A | 3/1990 | Hagiwara et al. |
| 4,938,958 A | 7/1990 | Niira et al. |
| 4,956,350 A | 9/1990 | Mosbey |
| 5,140,949 A | 8/1992 | Chu et al. |
| 5,144,016 A | 9/1992 | Skjak-Braek et al. |
| 5,146,932 A | 9/1992 | McCabe |
| 5,474,545 A | 12/1995 | Chikazawa |
| 5,482,932 A | 1/1996 | Thompson |
| 5,486,195 A | 1/1996 | Myers et al. |
| 5,502,042 A | 3/1996 | Gruskin et al. |
| 5,538,500 A | 7/1996 | Peterson |
| 5,556,699 A | 9/1996 | Niira et al. |
| 5,575,995 A | 11/1996 | Giovanoni |
| 5,578,022 A | 11/1996 | Scherson et al. |
| 5,597,581 A | 1/1997 | Kaessmann et al. |
| 5,599,578 A | 2/1997 | Butland |
| D386,002 S | 11/1997 | Hinkle |
| 5,696,101 A | 12/1997 | Wu et al. |
| 5,716,337 A | 2/1998 | McCabe et al. |
| 5,725,551 A | 3/1998 | Myers et al. |
| 5,728,451 A | 3/1998 | Langley et al. |
| 5,766,715 A | 6/1998 | Garconnet |
| 5,788,682 A | 8/1998 | Maget |
| 5,801,116 A | 9/1998 | Cottrell et al. |
| 5,826,543 A | 10/1998 | Raymond et al. |
| 5,855,570 A | 1/1999 | Scherson et al. |
| 5,891,074 A | 4/1999 | Cerarczyk |
| 5,916,511 A | 6/1999 | Kotani et al. |
| 5,941,897 A | 8/1999 | Myers |
| 5,964,239 A | 10/1999 | Loux et al. |
| 5,964,349 A | 10/1999 | Odagiri |
| 5,981,052 A | 11/1999 | Siguyama |
| 5,993,964 A | 11/1999 | Nakajima |
| 6,037,280 A | 3/2000 | Edwards et al. |
| 6,060,461 A | 5/2000 | Drake |
| 6,086,970 A | 7/2000 | Ren |
| 6,123,925 A | 9/2000 | Barry et al. |
| 6,159,232 A | 12/2000 | Nowakowski |
| 6,187,347 B1 | 2/2001 | Patterson et al. |
| 6,203,512 B1 | 3/2001 | Farris et al. |
| 6,251,423 B1 | 6/2001 | Bradford |
| 6,372,333 B1 | 4/2002 | Sugiyama et al. |
| 6,428,800 B2 | 8/2002 | Greenspan et al. |
| 6,450,537 B2 | 9/2002 | Norris |
| 6,475,470 B1 | 11/2002 | Kayane et al. |
| 6,481,134 B1 | 11/2002 | Aledo |
| 6,486,285 B2 | 11/2002 | Fujita |
| 6,495,367 B1 | 12/2002 | Isogawa et al. |
| 6,523,778 B2 | 2/2003 | Key et al. |
| 6,573,419 B2 | 6/2003 | Naimer |
| 6,590,337 B1 | 7/2003 | Nishikawa et al. |
| 6,622,856 B2 | 9/2003 | Gallo et al. |
| 6,630,140 B1 | 10/2003 | Grunstein |
| 6,638,073 B1 | 10/2003 | Kazimirov et al. |
| 6,685,227 B2 | 2/2004 | Merry et al. |
| 6,700,032 B1 | 3/2004 | Gray |
| 6,701,649 B1 | 3/2004 | Brosi |
| 6,745,720 B2 | 6/2004 | Rasner et al. |
| 6,890,177 B2 | 5/2005 | Dragan |
| 6,998,510 B2 | 2/2006 | Buckman et al. |
| 7,125,821 B2 | 10/2006 | Xu et al. |
| 7,303,759 B2 | 12/2007 | Mershon |
| 7,371,403 B2 | 5/2008 | McCarthy et al. |
| 7,429,252 B2 | 9/2008 | Sarangapani |
| 7,595,429 B2 | 9/2009 | Hursey |
| 7,604,819 B2 | 10/2009 | Huey et al. |
| 7,825,133 B2 | 11/2010 | Yi |
| 7,858,123 B2 | 12/2010 | Stucky |
| 7,968,114 B2 | 6/2011 | Huey et al. |
| 8,063,264 B2 | 11/2011 | Spearman et al. |
| 8,114,433 B2 | 2/2012 | Huey et al. |
| 8,202,532 B2 | 6/2012 | Huey et al. |
| 8,252,318 B2 | 8/2012 | Huey et al. |
| 8,252,344 B2 | 8/2012 | Hursey |
| 8,257,731 B2 | 9/2012 | Horn et al. |
| 8,257,732 B2 | 9/2012 | Huey et al. |
| 8,277,837 B2 | 10/2012 | Fischer et al. |
| 8,343,537 B2 | 1/2013 | Huey et al. |
| 8,383,148 B2 | 2/2013 | Huey et al. |
| 8,460,699 B2 | 6/2013 | Huey et al. |
| 8,512,743 B2 | 8/2013 | Horn et al. |
| 8,535,709 B2 | 9/2013 | Kennedy et al. |
| 8,557,278 B2 | 10/2013 | Huey et al. |
| 8,703,634 B2 | 4/2014 | Baker et al. |
| 8,784,876 B2 | 7/2014 | Huey et al. |
| 8,846,076 B2 | 9/2014 | Huey et al. |
| 8,938,898 B2 | 1/2015 | Lo et al. |
| 9,072,806 B2 | 7/2015 | Lo et al. |
| 9,078,782 B2 | 7/2015 | Huey et al. |
| 2002/0077653 A1 | 6/2002 | Hudson et al. |
| 2002/0141964 A1 | 10/2002 | Patterson et al. |
| 2002/0197302 A1 | 12/2002 | Cochrum et al. |
| 2003/0018357 A1 | 1/2003 | Luthra et al. |
| 2003/0133990 A1 | 7/2003 | Hursey et al. |
| 2003/0175333 A1 | 9/2003 | Shefer et al. |
| 2003/0176828 A1 | 9/2003 | Buckman et al. |
| 2003/0199922 A1 | 10/2003 | Buckman |
| 2003/0208150 A1 | 11/2003 | Bruder et al. |
| 2003/0212357 A1 | 11/2003 | Pace |
| 2004/0005350 A1 | 1/2004 | Looney et al. |
| 2004/0013715 A1 | 1/2004 | Wnek et al. |
| 2004/0038893 A1 | 2/2004 | Ladner et al. |
| 2004/0121027 A1 | 6/2004 | Pushpangadan et al. |
| 2004/0121438 A1 | 6/2004 | Quirk |
| 2004/0131820 A1 | 7/2004 | Turner et al. |
| 2004/0166172 A1 | 8/2004 | Rosati et al. |
| 2004/0166758 A1 | 8/2004 | Reichmann et al. |
| 2004/0169033 A1 | 9/2004 | Kuibira et al. |
| 2004/0243043 A1 | 12/2004 | McCarthy et al. |
| 2005/0023956 A1 | 2/2005 | Kwak et al. |
| 2005/0058721 A1 | 3/2005 | Hursey |
| 2005/0070693 A1 | 3/2005 | Hansen et al. |
| 2005/0074505 A1 | 4/2005 | Hursey |
| 2005/0107826 A1 | 5/2005 | Zhu et al. |
| 2005/0118230 A1 | 6/2005 | Hill et al. |
| 2005/0119112 A1 | 6/2005 | Pfenninger et al. |
| 2005/0137512 A1 | 6/2005 | Campbell et al. |
| 2005/0143689 A1 | 6/2005 | Ramsey, III |
| 2005/0147656 A1 | 7/2005 | McCarthy et al. |
| 2005/0246009 A1 | 11/2005 | Toner et al. |
| 2005/0248270 A1 | 11/2005 | Ghosh et al. |
| 2005/0249899 A1 | 11/2005 | Bonutti |
| 2005/0287239 A1 | 12/2005 | Joo et al. |
| 2006/0034935 A1 | 2/2006 | Pronovost et al. |
| 2006/0078628 A1 | 4/2006 | Koman et al. |
| 2006/0116635 A1 | 6/2006 | Van Heughten |
| 2006/0121101 A1 | 6/2006 | Ladizinsky |
| 2006/0127437 A1 | 6/2006 | Kennedy et al. |
| 2006/0141018 A1 | 6/2006 | Cochrum et al. |
| 2006/0141060 A1 | 6/2006 | Hursey et al. |
| 2006/0159733 A1 | 7/2006 | Pendharkar et al. |
| 2006/0172000 A1 | 8/2006 | Cullen et al. |
| 2006/0178609 A1 | 8/2006 | Horn et al. |
| 2006/0193905 A1 | 8/2006 | Ehringer et al. |
| 2006/0211965 A1 | 9/2006 | Horn et al. |
| 2006/0211971 A1 | 9/2006 | Horn et al. |
| 2006/0271094 A1 | 11/2006 | Hudson et al. |
| 2006/0282046 A1 | 12/2006 | Horn et al. |
| 2007/0016152 A1 | 1/2007 | Karpowicz et al. |
| 2007/0031515 A1 | 2/2007 | Stucky et al. |
| 2007/0065491 A1 | 3/2007 | Huey et al. |
| 2007/0104768 A1* | 5/2007 | Huey .................. A61L 15/18 424/443 |
| 2007/0104792 A1 | 5/2007 | Jenkins |
| 2007/0134293 A1 | 6/2007 | Huey et al. |
| 2007/0142783 A1 | 6/2007 | Huey et al. |
| 2007/0154509 A1 | 7/2007 | Wilcher et al. |
| 2007/0154510 A1 | 7/2007 | Wilcher et al. |

(56) References Cited

U.S. PATENT DOCUMENTS

| | | |
|---|---|---|
| 2007/0154564 A1 | 7/2007 | Stucky et al. |
| 2007/0160638 A1 | 7/2007 | Mentkow et al. |
| 2007/0160653 A1 | 7/2007 | Fischer et al. |
| 2007/0167971 A1 | 7/2007 | Huey et al. |
| 2007/0251849 A1 | 11/2007 | Lo et al. |
| 2007/0275073 A1 | 11/2007 | Huey et al. |
| 2007/0276308 A1 | 11/2007 | Huey et al. |
| 2007/0276345 A1 | 11/2007 | Huey et al. |
| 2007/0281011 A1 | 12/2007 | Jenkins et al. |
| 2008/0027365 A1 | 1/2008 | Huey |
| 2008/0085300 A1 | 4/2008 | Huey et al. |
| 2008/0097271 A1 | 4/2008 | Lo et al. |
| 2008/0125686 A1 | 5/2008 | Lo |
| 2008/0131855 A1 | 6/2008 | Eggert et al. |
| 2008/0145455 A1* | 6/2008 | Bedard .............. A61K 31/727 424/682 |
| 2008/0146984 A1 | 6/2008 | Campbell et al. |
| 2008/0199539 A1 | 8/2008 | Baker et al. |
| 2008/0206134 A1 | 8/2008 | Lo et al. |
| 2008/0254146 A1 | 10/2008 | Huey et al. |
| 2008/0254147 A1 | 10/2008 | Huey et al. |
| 2008/0269658 A1 | 10/2008 | Vinton et al. |
| 2008/0299226 A1 | 12/2008 | Mentkow et al. |
| 2008/0317831 A1 | 12/2008 | Lo |
| 2008/0319476 A1 | 12/2008 | Ward et al. |
| 2009/0008261 A1 | 1/2009 | Kotzeva et al. |
| 2009/0011394 A1 | 1/2009 | Meglan et al. |
| 2009/0018479 A1 | 1/2009 | McCarthy et al. |
| 2009/0043268 A1 | 2/2009 | Eddy et al. |
| 2009/0047366 A1 | 2/2009 | Bedard et al. |
| 2009/0053288 A1 | 2/2009 | Eskridge, Jr. et al. |
| 2009/0074880 A1 | 3/2009 | Ladizinsky |
| 2009/0076475 A1 | 3/2009 | Ross et al. |
| 2009/0112170 A1 | 4/2009 | Wells et al. |
| 2009/0123525 A1 | 5/2009 | Bedard |
| 2009/0155342 A1 | 6/2009 | Diegelmann et al. |
| 2009/0162406 A1 | 6/2009 | Basadonna et al. |
| 2009/0186013 A1 | 7/2009 | Stucky |
| 2009/0186071 A1 | 7/2009 | Huey et al. |
| 2009/0232902 A1 | 9/2009 | Liu et al. |
| 2009/0274769 A1 | 11/2009 | Fregonese |
| 2009/0299253 A1 | 12/2009 | Hursey |
| 2010/0035045 A1 | 2/2010 | McAmish |
| 2010/0079395 A1 | 4/2010 | Kim et al. |
| 2010/0121244 A1 | 5/2010 | Horn et al. |
| 2010/0184348 A1 | 7/2010 | McAmish |
| 2010/0209531 A2 | 8/2010 | Stucky et al. |
| 2010/0228174 A1 | 9/2010 | Huey |
| 2010/0233248 A1 | 9/2010 | Huey et al. |
| 2011/0015565 A1 | 1/2011 | Hursey |
| 2011/0059287 A1 | 3/2011 | McAmish |
| 2011/0064785 A1 | 3/2011 | Daniels |
| 2011/0150973 A1 | 6/2011 | Bowlin et al. |
| 2011/0229849 A1 | 9/2011 | Maurer et al. |
| 2011/0237994 A1 | 9/2011 | Russ et al. |
| 2011/0268784 A1 | 11/2011 | Huey |
| 2012/0004636 A1 | 1/2012 | Lo |
| 2012/0045742 A1 | 2/2012 | Meglan et al. |
| 2012/0070470 A1 | 3/2012 | Pahari |
| 2012/0130296 A1 | 5/2012 | Huey |
| 2012/0259262 A1 | 10/2012 | Huey |
| 2013/0041332 A1 | 2/2013 | Huey |
| 2013/0079695 A1 | 3/2013 | Huey |
| 2013/0178778 A1 | 7/2013 | Huey |
| 2013/0267923 A1 | 10/2013 | Huey |
| 2013/0344131 A1 | 12/2013 | Lo |
| 2014/0171848 A1 | 6/2014 | Huey et al. |
| 2014/0377362 A1 | 12/2014 | Pahari |
| 2015/0141301 A1* | 5/2015 | Rovison, Jr. ........... A01N 37/02 507/225 |
| 2015/0221238 A1 | 8/2015 | Huebner |
| 2015/0250918 A1 | 9/2015 | Dubey |
| 2016/0120901 A1 | 5/2016 | Basadonna |
| 2016/0193380 A1 | 7/2016 | Dubey |
| 2016/0213808 A1 | 7/2016 | Huey |
| 2017/0151365 A1 | 6/2017 | Dubey |

FOREIGN PATENT DOCUMENTS

| | | |
|---|---|---|
| CN | 101687056 | 3/2010 |
| CN | 201920992 U | 8/2011 |
| EP | 0 107 051 | 9/1983 |
| EP | 0 296 324 | 12/1988 |
| EP | 0 353 710 | 2/1990 |
| EP | 0 826 822 | 3/1998 |
| EP | 0 888 783 A1 | 7/1999 |
| EP | 1 159 972 A2 | 5/2001 |
| EP | 1 714 642 | 10/2006 |
| EP | 2 446 867 | 5/2012 |
| GB | 2 175 889 | 12/1986 |
| GB | 2 259 858 | 3/1993 |
| GB | 2 314 842 | 1/1998 |
| JP | S59-62050 | 9/1984 |
| JP | 61145120 | 7/1986 |
| JP | 01-096558 | 10/1987 |
| JP | 2-45040 | 2/1990 |
| JP | 9-504719 | 5/1997 |
| JP | 2777279 B2 | 7/1998 |
| JP | 10-337302 | 12/1998 |
| JP | 11-071228 | 3/1999 |
| JP | 11-178912 | 7/1999 |
| JP | 11-332909 A1 | 7/1999 |
| JP | 2002-530157 | 9/2002 |
| JP | 2002-331024 | 11/2002 |
| JP | 2003-66045 | 3/2003 |
| JP | 2003-305079 | 10/2003 |
| JP | 2005-015537 | 1/2005 |
| JP | 2004123651 | 7/2006 |
| WO | WO 92/19802 | 11/1992 |
| WO | WO 95/05445 | 2/1995 |
| WO | WO 95/12371 | 5/1995 |
| WO | WO 96/40285 | 12/1996 |
| WO | WO 99/13918 | 3/1999 |
| WO | WO 00/30694 | 6/2000 |
| WO | WO 00/66086 | 11/2000 |
| WO | WO 01/82896 | 8/2001 |
| WO | WO 01/97826 | 12/2001 |
| WO | WO 02/30479 | 4/2002 |
| WO | WO 02/060367 | 8/2002 |
| WO | WO 02/074325 | 9/2002 |
| WO | WO 03/057072 | 7/2003 |
| WO | WO 03/074566 | 9/2003 |
| WO | WO 2005/012493 | 2/2005 |
| WO | WO 2005/030279 | 4/2005 |
| WO | WO 2005/087280 | 9/2005 |
| WO | WO 2005/123170 | 12/2005 |
| WO | WO 2006/006140 | 1/2006 |
| WO | WO 2006/012218 | 2/2006 |
| WO | WO 2006/088912 | 8/2006 |
| WO | WO 2006/110393 | 10/2006 |
| WO | WO 2007/120342 | 10/2007 |
| WO | WO 2008/036225 | 3/2008 |
| WO | WO 2008/054566 | 5/2008 |
| WO | WO 2008/109160 | 9/2008 |
| WO | WO 2008/127497 | 10/2008 |
| WO | WO 2009/109194 | 9/2009 |
| WO | WO 2014/047436 | 3/2014 |

OTHER PUBLICATIONS

Analgesics and Anti-inflammatory agents 2004, retrieved from the internet on May 26, 2010, URL: http://web.archive.org/web/20040904151322/http://faculty.weber.edu/ewalker/Medicinal_Chemistry/topics/Analgesia_antiinflam/Analgesics_anti-inflammatory.htm.

Angeloni, V., M.D.: "How to care for your wound.", Heartland Dermatology & Skin Cancer P.C., copyright 2001, V. Angeloni MD.

Army halts use of new first aid item to study more, Seattle PI, Dec. 24, 2008.

Army halts use of WoundStat, http://stripes.com, Apr. 23, 2009.

Army pulls anti clotting agent after Fort Sam study finds threat, MySanAntonio Military, Dec. 24, 2008.

(56) References Cited

OTHER PUBLICATIONS

Baker, Sarah E. et al., Controlling Bioprocesses with Inorganic Surfaces: Layered Clay Hemostatic Agents, Department of Chemistry and Biochemistry, University of California, Santa Barbara, American Chemical Association 2007, 19, pp. 4390-4392 (3 pages total).
Basadonna, G., et al.: "A novel kaolin coated surgical gauze improves hemostasis both in vitro and in vivo", Journal of Surgical Research, vol. 144, No. 2, Feb. 2008, p. 440, XP002534658, abstract.
Bethesda, MD, TraumaCure, Life-saving News for Battlefield Soldiers & Wounded Civilians FDA Clears Product to Stop Severe Bleeding, Sep. 10, 2007.
Butenas—Mechanism of factor VIIa-dependent coagulation in hemophilia blood, Hemostasis, Thrombosis, and Vascular Biology, Blood, Feb. 1, 2002—vol. 99, No. 3.
Caloplast (Kaolin Poultrice), South African Electronic Package Inserts, Information presented by Malahide Information Systems, Copyright 1996-1998, printed from home.intekom.com/pharm/allied/caloplst.html#INDICATIONS, two pages.
Carraway, et al., Comparison of a new mineral based hemostatic agent to a commercially available granular zeolite agent for hemostasis in a swine model of lethal extremity arterial hemorrhage, Resuscitation vol. 78, Issue 2, Aug. 2008.
Clay makers (raw materials) retrieved from the internet on Mar. 15, 2010, URL: http://web.archive.org/web/20020609175053/http://www.claymaker.com/ceramic_central/info/raw_clays.htm (year 2002, pp. 104).
Comparative Testing of Hemostatic Dressings in a Severe Groin Hemorrhage, Trauma & Resuscitative Medicine Department, NMRC, Aug. 2008 (Part 2 of 3, pp. 10-19).
Comparative Testing of Hemostatic Dressings in a Severe Groin Hemorrhage, Trauma & Resuscitative Medicine Department, NMRC, Aug. 2008 (Part 3 of 3, pp. 20-29).
Comparative Testing of Hemostatic Dressings in a Severe Groin Hemorrhage, Trauma &Resuscitative Medicine Department, NMRC, Aug. 2008 (Part 1 of 3, pp. 1-9).
Connor, William E.: "The Acceleration of Thrombus Formatin by Certain Fatty Acids," Journal of Clinical Investigation, vol. 41, No. 6, 1962.
Curasorb Calcium Alginate Dressings information page, http://www.kendallhq.com/kendallhealthcare/pageBuilder.aspx?webPageID=0&topicID=70966&xsl=xsl/productPagePrint.xsl (last accessed May 22, 2012).
Davis et al., 1H—NMR Study of Na Alginates Extracted from Sargassum spp. in Relation to Metal Biosorption, 110 Applied Biochemistry and Biotechnology 75 (2003).
Dictionary of Traditional Chinese Medicine, "Astringents and Haemostatices," The Commercial Press, LTD., Apr. 1984 [ISBN 962 07 3051 8], pp. 216-217, total 4 pages.
Dyer, A. et al. "Diffusion in heteroionic zeolites: part 1. Diffusion of water in heteroionics natrolites." Microporous and Mesoporous Materials. 1998. pp. 27-38. vol. 21.
EPO Extended Search Report, re EP Application No. 12163455, dated Sep. 12, 2012.
Fruijtier-Polloth, "The safety of synthetic zeolites used in detergents", Arch Toxicol (2009) 83:23-25.
Galan, et al.: "Technical properties of compound kaolin sample from griva (Macedonia, Greece)", Applied Clay Science 1996 10:477-490.
Gibbar-Clements, et al.: "The Challenge of Warfarin Therapy", JSTOR: The American Journal of Nursing,vol. 100, No. 3 (Mar. 2000), pp. 38-40.
Gielen, M., Solid State Organometallic Chemistry: Methods and Applications Physical Organometallic Chemistry, 1999, New York John Wiley & Sons, Ltd. (UK), V. 2, p. 156.
Griffin, J. H.: "Role of surface in surface-dependent activation of Hageman factor (blood coagulation Factor XII)", Proc. Natl. Acad. Sci, USA, vol. 75, No. 4, pp. 1998-2002, Apr. 1978 Medical Sciences.
Griffin, John H., Role of surface in surface-dependent activation of Hageman factor (blood coagulation Factor XII), Proc. Natl. Acad. Sci. USA, vol. 75, No. 4, Apr. 1978, pp. 1998-2002 (5 pages total).
Hahn, Lynn: "High temperature 1H NMR to determine the relative amounts of guluronate and mannuronate in the sodium alginate sample", Intertek, ASA, Analytical Report, Report No. 60665 v 1, dated May 6, 2012.
HemCon Medical Technologies Inc. 501(k) Summary, ChitoGauze, Mar. 20, 2009.
Hempen, et al., A Materia Medica for Chinese Medicine, Plants minerals and animal products, Churchill Livingston Elsevier, 2009, [ISBN 978 0 443 10094 9], pp. 832-833 (Halloysitum rubrum, Chi shi zi), total 5 pages.
Hollister Wound Care Restore Calcium Alginate Dressing, Silver instruction manual and information booklet, available at http://hollisterwoundcare.com/files/pdfs/ifus/Restore907814B407ColorBreak.pdf (last accessed May 22, 2012).
Hsu, et al. Orintal Materia Medica—a concise guide, pp. 310-311, 612-613, 32-34, total 12 pages. Oriental Healing Arts Institute, 1986. [ISBN 0 941 942 22 8].
Huang, Pharmacology of Chinese Herbs, Second Edition, p. 243 (Antidiarrheal Herbs), total 3 pages. CRC Press 1999. [ISBN 0 8493 1665 0].
Hubbard, et al.: "Ionic charges of glass surfaces and other materials, and their possible role in the coagulation of blood," Journal of Applied Physiology, Mar. 1, 1960, vol. 15, No. 2, pp. 265-270.
IMA-EU, Kaolin, Oct. 2006, p. 1-2.
International Preliminary Report and Written Opinion for Application No. PCT/US2007/023265, dated Sep. 29, 2009.
International Preliminary Report and Written Opinion for PCT/US2004/029809, dated Mar. 13, 2006.
International Preliminary Report and Written Opinion re PCT/US2006/004594, dated Aug. 14, 2007.
International Preliminary Report and Written Opinion re PCT/US2008/006517, dated Nov. 24, 2009.
International Preliminary Report and Written Opinion Report for Application No. PCT/US2008/060177, dated Oct. 13, 2009.
International Report on Patentability and Written Opinion for Application No. PCT/US2008/003082, dated Sep. 29, 2009.
International Search Report for Application No. PCT/US2004/029812, dated Jun. 14, 2005.
International Search Report for Application No. PCT/US2006/004594, dated Nov. 3, 2006.
International Search Report for Application No. PCT/US2006/012487, dated Sep. 12, 2006.
International Search Report for Application No. PCT/US2007/016509, dated Feb. 8, 2008.
International Search Report for Application No. PCT/US2007/023265, dated Sep. 17, 2009.
International Search Report for Application No. PCT/US2008/003082, dated Sep. 24, 2009.
International Search Report for Application No. PCT/US2008/060177, dated Jun. 22, 2009.
International Search Report for Application No. PCT/US2008/075191, dated Oct. 6, 2008.
International Search Report for PCT/US2004/029809, dated Feb. 24, 2005.
International Search Report for PCT/US2005/046700, dated Jul. 6, 2006.
James, "Silver Copper Zeolite Guinea Pig Sensitization Study—Buehler Method", Data Evaluation Report dated Oct. 3, 1989.
Kheirabadi, Army Assessment of New Hemostatic Products Suitable for Treating Combat Wounds, US Army Institute of Surgical Research, Aug. 11, 2008.
Kheirabadi, et al., Session IV-B, Paper 28, 8:20 a.m., Comparison of New Hemostatic Dressings with Currently Deployed Hemcon Bandage in a Model of Extremity Arterial Hemorrhage in Swine, Jan. 2009.
Kheirabadi, et al., The Journal of Trauma Injury, Infection, and Critical Care, Comparison of New Hemostatic Granules/Powders with Currently Deployed Hemostatic Products in a Lethal model of Extremity Arterial Hemorrhage in Swine, Feb. 2009, pp. 316-328.

(56) References Cited

OTHER PUBLICATIONS

Kheirabadi, Final Report, Title: Assessment of Efficacy of New Hemostatic Agents in a Model of Extremity Arterial Hemorrhage in Swine, U.S. Army Institute of Surgical Research, Ft. Sam Houston, TX 78234, Mar. 4, 2008.
Kovzun, I. G., et al.: "Application of nanosize clay-mineral systems in the complex therapy for hemophilia "A" patients", Database HCAPLUS [online], XP002534657, retrieved from STN Database accession No. 2009:502758 abstract & Nanosistemi, Nanomateriali, Nanotekhnologii, vol. 6, No. 2, 2008.
Le Van Mao, Raymond et al. "Mesoporous Aluminosilicates prepared from Zeolites by Treatment with Ammonium Fluorosilicate." J. Mater. Chem. 1993. pp. 679-683. vol. 3, No. 6.
Li, et al. Chinese Materia Medica—Combinations and Applications, Donica Publishing Ltd., 2002, [ISBN 1 901149 02 1], p. 622 (Ch. 18 Herbs for Promoting Astriction), total 5 pages.
Lin et al., Synthesis of Hybridized Polyacrylic Acid-Kaolin Material and Its Superwater Absorbent Performance, J. Huaqiao Univ. (Nat. Sci.) Mar. 2000.
Long et al., Synthesis of Bentonite-superabsorbent Composite, J. Guilin Inst. Tech., Feb. 2004.
Macrina, VCU's Research Enterprise, Structure and Resources, Oct. 23, 2008.
Manugel® GMB alginate, FMC BioPolymer, Know how. It works. sm Product Specifications, 2011 FMC Corporation.
Margolis, "Initiation of Blood Coagulation by Glass and Related Surfaces", J. Physiol. (1957) 137, 95-109.
Margolis, J., The Kaolin Clotting Time: A Rapid One-Stage Method for Diagnosis of Coagulation Defects, J. Clin. Pathol 1958, 11, pp. 406-409 (5 pages total).
Medline Maxorb Extra AG Silver Alginate, http://www.medicaldepartmentstore.com/Medline-Maxorb-p/1560.htm (last accessed May 22, 2012).
Okada, et al.: "Preparation of zeolite-coated cordierite honeycombs prepared by an in situ crystallization method", Science and Technology of Advanced Materials 2004 5:479-484.
O'Reilly et al.: "Studies on Coumarin Anticoagulant Drugs—Initiation of Warfarin Therapy Without a Loading Dose", Circulation by the American Heart Association, http://circ.ahajournals.org, 1968, 38, 169-177.
Ore-Medix, Traumastat Hemostatic Bandage, Aug. 7, 2008.
PCT International Report on Patentability and Written Opinion re PCT/US2009/040256, dated Oct. 12, 2010.
PCT International Search Report re Application No. PCT/US2010/041741, dated Nov. 26, 2010.
PCT International Search Report re PCT/US2009/040256, dated Aug. 4, 2009.
Permanent suspension of Woundstat use, https://email.z-medica.com, Apr. 17, 2009.
Reprinted related contents of U.S. Abstract regarding QuikClot Combat Gauze, Apr. 2009.
Ross, et al., "The Kaolin Minerals," J. Amer. Ceramic Soc., vol. 13, issue 3, pp. 151 to 160, Mar. 1930.
Sadler et al.: "Biochemistry and Genetics of Van Willebrand Factor", Annual Review of Biochemistry; 1998. 67:395-424.
Scott Sackinger's Medical Devices Professional Summary dated Mar. 2009.
Sinter. (2004). In the New Penguin Dictionary of Science. London: Penguin. Retrieved May 7, 2009, from http://www.credoreference.com/entry/7463549/.
Soine et al., Roger's Inorganic Pharmaceutical Chemistry, Lea & Febiger 1967, p. 462-463 (Aluminum and Aluminum Compounds), [QV744 S683r 1967] total 5 pages.
Tactical Combat Casualty Care Guidelines, Feb. 2009.
The Merck Index; 1989, pp. 1596-1597, abstract 10021.
Top, Ayben et al. "Silver, zinc, and copper exchange in a Na-clinoptilolite and resulting effect on antibacterial activity." Applied Clay Science. 2004. pp. 13-19. vol. 27.
TraumaCure, Innovative Wound Care Products for Wound Care Solutions, Apr. 24, 2009.

U.S. Appl. No. 12/352,513, filed Jan. 12, 2009 including prosecution history.
U.S. Appl. No. 12/611,830, filed Nov. 3, 2009, including prosecution history.
U.S. Appl. No. 13/175,380, filed Jul. 1, 2011, including prosecution history.
U.S. Appl. No. 13/526,431, filed Jun. 18, 2012 including prosecution history.
U.S. Appl. No. 13/593,310, filed Aug. 23, 2012, including prosecution history.
U.S. Appl. No. 13/595,932, filed Aug. 27, 2012, including prosecution history.
U.S. Appl. No. 13/598,381, filed Aug. 29, 2012, including prosecution history.
U.S. Appl. No. 13/682,085, filed Nov. 20, 2012, including prosecution history.
U.S. Appl. No. 13/759,963, filed Feb. 5, 2013, including prosecution history.
U.S. Appl. No. 13/911,616, filed Jun. 6, 2013, including prosecution history.
U.S. Appl. No. 13/922,115, filed Jun. 19, 2013, including prosecution history.
U.S. Appl. No. 60/668,022, filed Apr. 4, 2005, including prosecution history.
U.S. Appl. No. 60/708,206, filed Aug. 15, 2005, including prosecution history.
U.S. Appl. No. 60/902,738, filed Feb. 21, 2007, including prosecution history.
U.S. Appl. No. 60/955,854, filed Aug. 14, 2007, including prosecution history.
US Office Action (Final) re U.S. Appl. No. 12/140,356, filed Jun. 17, 2008, Office Action dated Mar. 21, 2011.
US Office Action re U.S. Appl. No. 11/398,161 dated Apr. 30, 2008.
US Office Action re U.S. Appl. No. 11/634,673, filed Dec. 5, 2006, Office Action dated Nov. 14, 2008.
Vitrify—(2001). In Chambers 21st Century Dictionary. London. Chambers Harrap. Retrieved May 7, 2009, from http://www.credoreference.com/entry/1236485/.
Vlok, Marie E.: "Kaolin poultice", Manual of Nursing, vol. 1, Basic Nursing, revised ninth edition, p. 269. Copyright Juta & Co, Ltd., Lansdowne, South Africa, first published 1962.
Voet, Donald & Judith: "Molecular Physiology", Biochemistry, p. 1087-1096, vol. 64, 1990, John Wiley & Sons.
Wagner, Holly, "Topical Oxygen Helps Hard-To-Heal Wounds Heal Faster and Better," Jan. 28, 2003, obtained from http://researchnews.osu.edu/archive/oxywound.htm.
Ward, et al., The Journal of Trauma Injury, Infection, and Critical Care, Comparison of a New Hemostatic Agent to Current Combat Hemostatic Agents in a Swine Model of Lethal Extremity Arterial Hemorrhage, Aug. 2007, pp. 276-284.
Webster's Dictionary definition of "expose" (1993).
Wound Stat, http://shadowspear.com/vb/showthread.php?t=16586 dated Dec. 22, 2008, last accessed Apr. 16, 2009.
WoundStat found to be potentially hazardous, Army News, news from Iraq . . . . , http://armytimes.com/news/2009/04/army_woundstat_042009w/, posted Apr. 20, 2009, last accessed Apr. 20, 2009.
Wright, J. Barry et al.: "Wound management in an era of increasing bacterial antibiotic resistance: A role for topical silver treatment", American Journal of Infection Control, vol. 26 (6), 1998, pp. 572-577.
Wright, J.K. et al. "Thermal Injury Resulting from Application of a GranularMineral Hemostatic Agent." The Journal of Trauma Injury, Infection, and Critical Care. 2004. pp. 224-230. vol. 57, No. 2.
Wu, Jing-Nuan, "An Illustrated Chinese Materia Medica," Oxford University Press, Inc. 2005 (13 pages).
Xinrong, Traditional Chinese Medicine, A Manual from A-Z, Symptoms, Therapy and Herbal Remedies, [ISBN 3 540 42846 1], p. 470 (total 3 pages), Springer-Verlag Berlin Heidelberg 2003.
Yanchi, The Essential Book of Traditional Chinese Medicine, vol. 2: Clinical Practice, p. 155-157 (Traditional Chinese Prescriptions), 142-143 (Chinese Medicinal Herbs) total 8 pages. [ISBN 0 231 06518 3 9v.2] 1988.

(56) References Cited

OTHER PUBLICATIONS

Z-Medica Corporation 510(k) Summary, QuikClot eX, Oct. 4, 2007.
Oh, Seung-Taek et al.: "The Preparation of Plyurethane Foam Combined with pH-sensitive Alginate/Bentonite Hydrogel for Wound Dressings," Fibers and Polymers 2011, vol. 12. No. 2, 159-165.
Reprinted related contents US ALARACT re Quikclot Sep. 2008.
Revised Pharmaceutical Product Additive Handbook, Yakuji Hosha Inc., Feb. 28, 2007, first printing, p. 41-44.
Miyajima, C., General Information on Alginates and its Applications, Sen'i Gakkaishi (Fibers and Industry), 2009, pp. 444-448, vol. 65, No. 12.
U.S. Appl. No. 15/071,520, filed Mar. 16, 2016, including prosecution history.
U.S. Appl. No. 14/643,689, filed Mar. 10, 2015, including prosecution history.
U.S. Appl. No. 15/090,072, filed Apr. 4, 2016 including prosecution history.
Acheson, et al.: "Comparison of Hemorrage Control Agents Applied to Lethal Extremity Arterial Hemorrages in Swine," The Journal of TRAUMA, Injury, Infection, and Critical Care, 2005:59 865-875.
Dubick et al.: "New Technologies for Treating Severe Bleeding in Far-Forward Combat Areas," RTO-MP-HFM-182, 21-1 to 21-12.
NATO/OTAM, U.S. Army Institute of Surgical Research (Apr. 2010 according to http://www.dtic.mil/docs/citations/ADA581701).
Handbook of textile fibre structure, First Published 2009, Cover pages and p. 276, (total 5 pages).
Pusateri, et al.: "Application of a Granular Mineral-Based Hemostatic Agent (QuickClot) to Reduce Blood Loss After Grade V Liver Injury in Swine," The Journal of TRAUMA, Injuary, Infection, and Critical Care, 2004:57 555-562.
Pusateri, et al.: "Effect of a Chitosan-Based Hemostatic Dressing on Blood Loss and Survival in a Model of Sever Henous Hemorrage and Hepatic Injury in Swine," The Journal of TRAUMA, Injury, Infection, and Critical Care, 2003: 54 177-182.
Stasilon, Wikipedia—definition (printed 2011).
Traditional Chinese Medicine, A Manual from A-Z. Symptoms, Therapy and Herbal Remedies, cover pages plus p. 470, total 3 pages, Springer-Verlag Berlin Heidelberg 2003.
U.S. Appl. No. 15/429,935 filed Feb. 10, 2017 including prosecution history.
U.S. Appl. No. 15/641,999 filed Jul. 5, 2017 including prosecution history.
Ward, Declaration and CV, signed Jul. 19, 2012.
Yanchi, Liu: "Drug Forms: Their Administration and Actions," The Essential Book of Traditional Chinese Medicine, cover pages plus pp. 142, 143, 155-157, and 468, total 8 pages, 7, vol. 2: Clinical Practice. 1988.

\* cited by examiner

HEMOSTATIC COMPOSITIONS, DEVICES, AND METHODS

CROSS REFERENCE TO RELATED APPLICATIONS

The present application is a continuation of U.S. patent application Ser. No. 14/479,214, filed Sep. 5, 2014, now pending, which is a continuation of U.S. patent application Ser. No. 13/240,795, filed Sep. 22, 2011, now U.S. Pat. No. 8,858,969, which claims the priority benefit of U.S. Patent Application No. 61/385,388, filed Sep. 22, 2010. These applications and any other applications for which a foreign or domestic priority claim is identified in the Application Data Sheet filed with the present application are hereby incorporated by reference for all purposes in their entireties herein under 37 C.F.R. § 1.57.

BACKGROUND OF THE INVENTION

Field of the Invention

The disclosed embodiments relate to compositions, devices, and methods related to promoting blood clotting.

Description of the Related Art

Blood is a liquid tissue that includes red cells, white cells, corpuscles, and platelets dispersed in a liquid phase. The liquid phase is plasma, which includes acids, lipids, solubilized electrolytes, and proteins. The proteins are suspended in the liquid phase and can be separated out of the liquid phase by any of a variety of methods such as filtration, centrifugation, electrophoresis, and immunochemical techniques. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, wounds can be inflicted as the result of trauma. Often bleeding is associated with such wounds. In some circumstances, the wound and the bleeding are minor, and normal blood clotting functions in addition to the application of simple first aid are all that is required. First aid may include applying pressure to the wound with a sponge or similar device to facilitate clotting functions. Unfortunately, however, in other circumstances substantial bleeding can occur. Bleeding can also be a problem when the trauma is the result of a surgical procedure. Apart from suturing or stapling an incision or internally bleeding area, bleeding encountered during surgery is often controlled using sponges or other materials used to exert pressure against the bleed site and/or absorb the blood. However, in many circumstances these measures are not sufficient, such as when the bleeding becomes excessive, or when the wound is difficult to reach, or when it is advantageous to be able to view continuously the wound area.

SUMMARY OF THE INVENTION

Compositions comprising a clay, or a component of a clay, dispersed in a liquid medium can be useful as hemostatic or blood-clotting compositions or agents. These compositions may be useful for promoting the clotting of blood for animals or human beings, including clotting blood in individuals with a compromised ability to clot blood, such as individuals taking anticoagulant drugs such as heparin, warfarin, clopidogrel, coumarin, etc., or individuals suffering from clotting disorders such as Hemophilia A, Hemophilia B, von Willebrand disease, etc.

Some embodiments include a blood-clotting agent comprising: a composition comprising clay dispersed in a liquid medium, wherein the clay is less than about 10% by weight of the composition; and wherein the composition including the liquid medium and clay has a viscosity of about 1000 cP or less.

Some embodiments include a blood-clotting agent comprising: a composition comprising clay dispersed in a liquid medium, wherein the clay is less than about 10% by weight of the composition; and wherein the composition including the liquid medium and clay has a viscosity of about 1000 cP to about 100,000 cP.

Some embodiments include a hemostatic composition comprising: a clay dispersed in an aqueous medium; wherein the composition is a liquid which is substantially free of visible clay particles; and wherein the composition is sterilized.

Some embodiments comprise a hemostatic composition comprising: kaolin dispersed in an aqueous medium; wherein the composition is flowable; wherein at least 50% of the kaolin has a particle size in the range of about 1 nm to about 1000 nm; and wherein the composition is sterilized.

Some embodiments include a hemostatic device comprising: a vessel which contains a hemostatic composition of the type described herein; and a dispensing component in fluid communication with the vessel; wherein the device is configured so that the dispensing component is capable of dispensing the hemostatic composition from the vessel to a bleeding area of an animal or person.

Some embodiments comprise a hemostatic composition comprising: a liquid comprising a first component of a kaolin, wherein the first component of the kaolin is prepared by a process comprising: dispersing the kaolin in an aqueous medium; and separating the first component of the kaolin from a second component of the kaolin; wherein the first component of the kaolin has an average particle size which is smaller than an average particle size of the second component of kaolin.

Some embodiments include a hemostatic composition comprising: a component of kaolin dispersed in an aqueous medium; wherein the component of kaolin is capable of remaining dispersed in the aqueous medium for at least about 60 minutes without agitation.

Some embodiments include a hemostatic composition comprising: a component of kaolin dispersed in an aqueous medium; wherein the component of kaolin is capable of remaining dispersed in the aqueous medium for at least about 5 minutes in a centrifuge at a centripetal acceleration of at least about 1000 m/s$^2$.

Some embodiments include a blood-clotting composition comprising: a fine kaolin having a reduced particle size as compared to a particle size of a naturally and/or commonly occurring kaolin; and water; wherein the fine kaolin is dispersed in the water to form a stable kaolin-water dispersion.

Some embodiments include a hemostatic system comprising: a hemostatic device comprising: a vessel comprising an interior volume configured to contain a liquid; an orifice in fluid communication with the interior volume comprising a rim surrounding the orifice, wherein the rim is configured to form a seal, a removable adhesive connection, or a contact surface with a part of an animal body or a human body; a fluid input component configured to provide a liquid to the interior volume of the vessel; and a fluid output component configured to allow liquid to exit the interior volume of the vessel; and a composition of the type described herein.

DETAILED DESCRIPTION OF THE PREFERRED EMBODIMENT

As used herein, the term "hemostatic composition" is used in accordance with the ordinary meaning in the art and includes a blood-clotting agent, a blood-clotting composition, a hemostatic composition, a hemostatic agent, or a similar material. A hemostatic composition may comprise a clay or a component of a clay which may be dispersed in a liquid medium.

A liquid medium may include any liquid, including an aqueous liquid. In some embodiments, the liquid medium may contain at least: about 10%, about 50%, or about 90% water by weight. Other liquids, including organic liquids, may be used. For example, alcohols such as glycerin, ethanol, methanol, isopropanol, and the like, may also be used. A combination of non-aqueous liquids or a combination of water and other liquids may also be used. In some embodiments, tap water, saline water, distilled water, or sterile water may be used.

A clay may include any clay such as kaolin, bentonite, montmorillonite, saponite, polygorskite or attapulgite, sepiolite, etc. In some embodiments, the clay may be a kaolin clay, which may include the mineral "kaolinite." The kaolin may include Edgar's plastic kaolin (hereinafter "EPK"), which is a water-washed kaolin clay that is mined and processed around Edgar, Fla.

A hemostatic composition may be prepared by adding an appropriate amount of clay to a liquid. This mixture may be used with these constituents by themselves and/or without further treatment or processing (besides possibly sterilization). In some embodiments, the mixture may be subjected to a separation process which may produce a separation of the clay into components or may provide clay particles in particular ranges of sizes. Thus, in some embodiments, one or more components or particular size ranges of clay may be used in addition to or in place of a native or standard type of clay. The component or particular size range of clay may be obtained by a separation process or may be separately obtained and added to a liquid. As used herein, unless otherwise indicated, the term "clay" should be understood to include clay, a component of clay, or a combination thereof.

In some embodiments, a first component of a clay may be separated from a second component of a clay. One or more separation processes may further provide additional components of the clay, such as a third component, a fourth component, etc. An example of a method that may be used to accomplish a separation may be dispersing a clay in a liquid, and then separating the dispersion by filtration or using one or more settling methods such as centrifugation or standing.

A separation may produce a first component which is distinct from other components in some way. Some separations involve separating a fraction which has more liquid from a fraction which has more solid, as compared to the composition before the separation is carried out. A liquid fraction may include a supernatant, or the liquid portion removed from the top of a centrifuged mixture, or a filtrate, or the liquid which is passed through a filter during a filtration. A solid fraction may include the sediment or solid material from a centrifugation or the filtered solid material obtained by filtration. In some embodiments, a first component of a clay is separated from a second component of a clay by centrifuge or filtration.

In some embodiments, a first component may consist essentially of or include higher levels of ions of calcium (e.g. $Ca^+$, $Ca^{2+}$, etc.), aluminum (e.g. $Al^+$, $Al^{2+}$, $Al^{3+}$, etc.), iron (e.g. $Fe^+$, $Fe^{2+}$, $Fe^{3+}$, etc.) magnesium (e.g. $Mg^+$, $Mg^{2+}$, etc.), potassium (e.g. $K^+$), sodium (e.g. $Na^+$), or other ions. If the first component comprises a liquid fraction, this may be because the ions are soluble in the liquid, and thus retained with the liquid fraction. For example, the molar ratio of one or more of these ions in a first component as compared to a second component may be at least about 1.1, about 2, or about 5 to about 10, about 100, or about 1000. Ions such as those listed above may also be added directly to the composition.

In some embodiments, a first component may have an average particle size which is smaller than the average particle size of a second component or another component of the clay.

While a clay may be present in any amount, a clay may be at least: about 0.00001%, about 0.001%, or about 0.01% by weight of the composition, and/or may further be about 10% or less, about 5% or less, or about 1% or less by weight of the composition. In some embodiments, a hemostatic composition may include clay particles of a size that renders the composition substantially free of visible clay particles to an observer with an unaided eye. In some embodiments, the turbidity of the composition may be at least: about 0.001 Nephelometric Turbitidy Units (NTU), about 0.01 NTU, or about 0.3 NTU, and/or may further be about 5 or less, about 50 or less, or about 200 or less. In some embodiments, the clay may be dispersed in a liquid to provide a stable clay-liquid dispersion, such as a stable clay-water dispersion or kaolin-water dispersion. In some embodiments, an appreciable amount of the clay particles may not settle from an aqueous liquid upon standing. In some embodiments, the clay particles may not settle from an aqueous liquid upon standing for at least about 5 minutes, at least about 1 hour, at least about 12 hours, at least about 1 day, at least about 1 month, or at least about 1 year. In some embodiments, the clay particles may be capable of remaining dispersed in an aqueous liquid for at least about 1 minute, at least about 5 minutes, at least about 30 minutes, or at least about an hour in a centrifuge at a centripetal acceleration of at least about 100 m/s, at least about 1000 m/s, or at least about 10,000 m/s.

A clay may have a particle size in a range that allows it to be dispersed in the liquid. For example, in some embodiments, at least about 50%, at least about 90%, or at least about 95% of a clay, such as kaolin, may have a particle size in the range of about 1 nm to about 10 μm, about 10 nm to about 5 μm, or about 50 nm to about 5 μm. In some embodiments, a fine clay may be used which has a reduced particle size as compared to a particle size of a naturally and/or commonly occurring clay. In some embodiments, the fine clay may be fine kaolin.

Tonicity agents may be included or omitted in a hemostatic composition to adjust tonicity, for example, to make the composition isotonic, hypertonic, or hypotonic. Tonicity may be adjusted by adjusting the concentration of a tonicity agent. For example, reducing the concentration of a tonicity agent may reduce the tonicity of the composition, and increasing the concentration of a tonicity agent may increase the tonicity of the composition. Suitable tonicity agents include, but are not limited to, sugars, such as glucose and isomers thereof, dextrose, fructose and isomers thereof, disaccharides, etc.; alkali salts (e.g. Group I salts), such as salts of $Na^+$, $K^+$, etc.; halide salts, such as salts of $Cl^-$, $Br^-$, $I^-$, etc.; polyols such as glycerin and other sugar alcohols such as mannitol, sorbitol, etc.; etc.

A hemostatic composition may be sterile or sterilized. An antimicrobial agent may be included in some embodiments, which may help to preserve the sterility of a composition over time, or may help to improve or preserve the sterility of the bleeding area while a hemostatic composition is used to promote clotting of a wound. Suitable antimicrobial agents may include, but are not limited to, compounds or salts containing silver ions; compounds or salts containing copper ions; and halogen-based antimicrobials such as iodine, bromine, and chlorine, and salts or oxides thereof, such as $ClO^-$, $BrO^-$, $IO^-$, etc. In some embodiments, the antimicrobial agent may comprise a stabilized halogen or halogen containing salt. One example of an antimicrobial agent includes povidone (also known as polyvinylpyrrolidone) and/or iodine, such as a 10% povidone iodine solution.

A hemostatic composition may comprise a therapeutically active agent. Examples of therapeutically active agents may include, but are not limited to, analgesics, including but not limited to, opiates such as codeine, morphine, oxycodone, etc.; acetaminophen; anti-inflammatory agents, including nonsteroidal anti-inflammatory drugs, aspirin, etc.; antibiotics or another antimicrobial drugs or compounds; antihistamines (e.g., cimetidine, chlorpheniramine maleate, diphenhydramine hydrochloride, and promethazine hydrochloride); antifungal agents; ascorbic acid; tranexamic acid; rutin; thrombin; botanical agents; etc.; and combinations thereof. Other additives may include magnesium sulfate, sodium metaphosphate, calcium chloride, dextrin, and combinations thereof.

A hemostatic agent may be in any form, such as a liquid, a gel, a paste, a foam, a cream, a particle, a powder, or other form. In some embodiments, a hemostatic composition may be flowable. For example, a hemostatic composition may have a viscosity from at least: about 0.1 cP, about 0.2 cP, about 0.5 cP, about 1 cP; and/or less than or equal to: about 1000 cP, about 10,000 cP, or about 100,000 cP. The viscosity may vary according to the type of injury or situation in which the composition is used and/or the form of the composition. For example, in some embodiments, a liquid with a viscosity similar to water, such as a viscosity at or below about 1000 cP, about 100 cP, or about 10 cP, may be desired for surgical applications. In some situations, such as in treating a wound formed by a bullet or another type of penetrating wound, a form of composition that is thicker or more viscous than water may be used, such as a gel or foam, to allow the composition to generally plug up or generally fill or generally obstruct or generally impede communication between the internal injured area and the area outside of the body to diminish the egress of blood from the wound and the ingress of contaminants into the wound. The composition may, in some instances, have much higher viscosities, such as at least: about 1000 cP, about 10,000 cP, or about 50,000 cP; and/or less than or equal to: about 100,000 cP, about 150,000 cP, or about 250,000 cP.

For some forms of thicker or more viscous compositions, such as gels, pastes, foams, or other forms, a thickening agent, such as a gelling agent, may be added to increase the viscosity of the liquid. The thickening agent may also help to keep a hemostatic agent such as a clay from settling from the dispersion. Any thickening agent may be used, including, but not limited to, cellulose derivatives such as carboxymethylcellulose, hydroxypropylmethylcellulose, methylcellulose, hydroxypropylcellulose, etc.; other carbohydrates or polysaccharides, or derivatives thereof, such as dextrans, starches, starch derivatives, carrageenan, guar gum, gum karaya, xanthan gum, gum arabic, gum tragacanth, etc.; polycarboxylic acids such as polyacrylic acid, polymethacrylic acid, etc.; fatty acids such as myristic acid, palmitic acid, stearic acid, arachidic acid, and behenic acid, palmitoleic acid, oleic acid, linoleic acid, α-linolenic acid, γ-linolenic acid, arachidonic acid, eicosapentaenoic acid, etc.; polyalkylene glycol polymers or copolymers such as polyethylene glycol, polyethylene glycol-polypropylene glycol copolymers, etc.

A hemostatic composition may also contain cations such as calcium (e.g. $Ca^+$, $Ca^{2+}$, etc.), aluminum (e.g. $Al^+$, $Al^{2+}$, $Al^{3+}$, etc.), iron (e.g. $Fe^+$, $Fe^{2+}$, $Fe^{3+}$, etc.) magnesium (e.g. $Mg^+$, $Mg^{2+}$, etc.), potassium (e.g. $K^+$), sodium (e.g. $Na^+$), silver, etc.

A hemostatic composition may be applied to any bleeding area of an animal or human being. Examples of injuries which may involve bleeding which could be treated with a hemostatic composition include, but are not limited to, injuries related to surgery, injuries caused by a weapon such as a bullet, a blade such as a knife, sword or bayonet, an explosive weapon, etc.

In some situations, such as in treating an injury characterized by a generally long, generally tube-shaped bleeding hole (e.g., a bullet track or an injury caused by a biopsy), treatment may be accomplished by applying slightly more pressure to the infused hemostatic liquid than that of the exiting blood to position the hemostatic material at a suitable location within or proximate to the injury to assist in diminishing or halting bleeding. For example, the pressure may be at least: about 180 mmHg, about 200 mmHg, about 250, about 300 mmHg; and/or less than or equal to: about 500 mmHg, about 700 mmHg, or about 1000 mmHg. In some embodiments, the pressure may be about 300 mmHg.

The term "vessel" is used herein in accordance with its ordinary meaning in the art and includes any structure which is capable of holding a hemostatic composition and being in fluid communication with a dispensing component. Examples may include, but are not limited to, containers such as bottles, vials, canisters, tubes, reservoirs, etc., and materials which may hold the composition such as a sponge, a cloth, a gauze, etc. A dispensing component may be any feature which is capable of being in fluid communication with a vessel and dispensing a hemostatic composition from the vessel to a bleeding area of an animal or person. Examples may include, but are not limited to, valves, lumens, orifices, pumps, sponges, cloths, etc. In some embodiments, a hemostatic device may comprise an absorbent material, such as a sponge, cloth, gauze, etc., wherein a liquid hemostatic composition is absorbed therein. The absorbent material may be saturated, meaning that the material cannot absorb any more liquid, or it may contain a liquid hemostatic composition but not be saturated. These devices may be further packaged in a film or other sealing material to reduce evaporation or other loss of the liquid.

Figure 1:
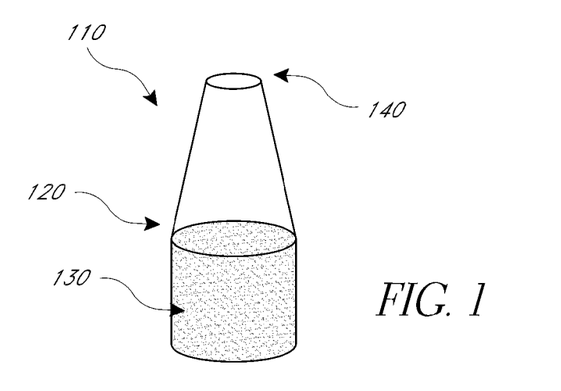
FIG. 1 depicts a schematic example of a hemostatic device.

A hemostatic composition may be dispensed by and/or incorporated into a hemostatic device. FIG. 1 depicts a schematic example of an embodiment of a hemostatic device 110 which may comprise a vessel 120 which contains a hemostatic composition 130 and a dispensing component 140 in fluid communication with the vessel 120. In this example, the device is configured so that the dispensing component is capable of dispensing the hemostatic composition from the vessel to a bleeding area of an animal or person.

Figure 2A:
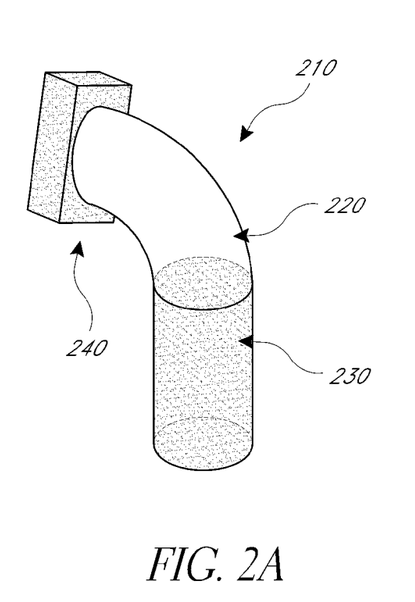
FIG. 2A depicts another schematic example of a hemostatic device.

FIG. 2A depicts another example of an embodiment of a hemostatic device 210. In this example, the vessel 220 may have a handle shape and may contain a liquid hemostatic composition 230. The vessel 220 may be connected to a dispensing component 240 comprising an absorbent material such as a sponge, which may be applied directly to the bleeding area.

Figure 2B:
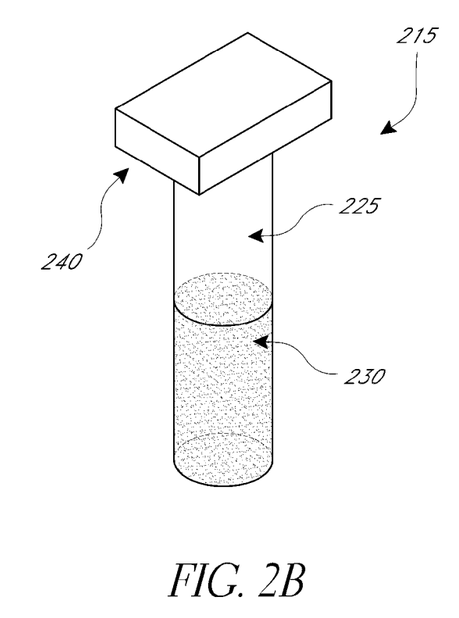
FIG. 2B depicts another schematic example of a hemostatic device.

FIG. 2B depicts yet another example of an embodiment of a hemostatic device 215. In this example, the vessel 225 may comprise a cylinder and may contain a liquid hemostatic composition 230. The vessel 225 may be connected to a dispensing component 240 comprising an absorbent material such as a sponge, which may be applied directly to the bleeding area.

Figure 3:
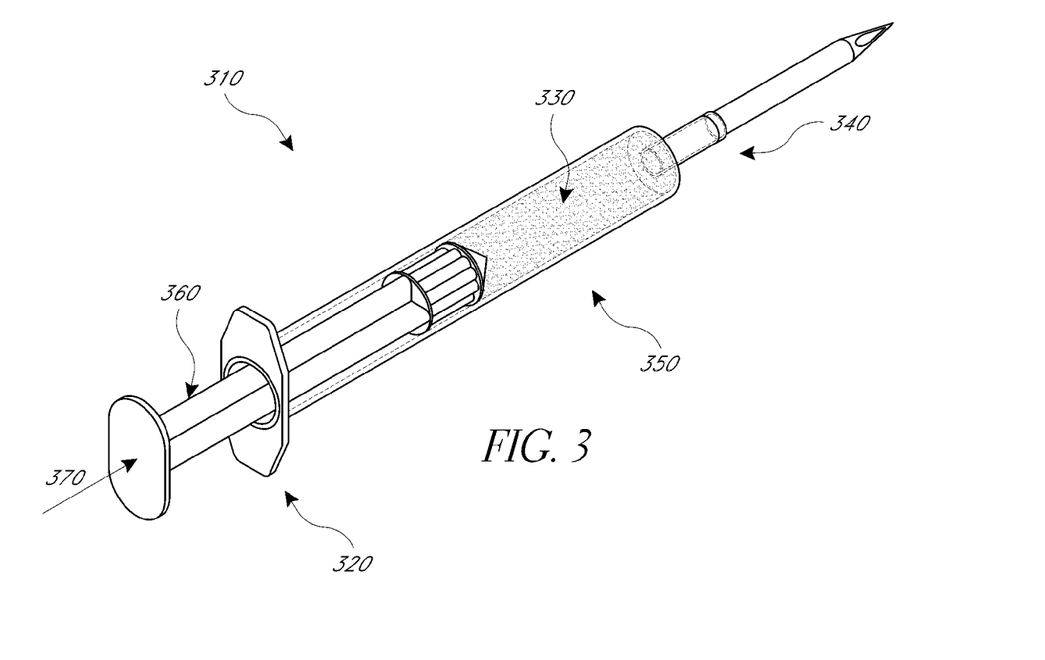
FIG. 3 depicts another schematic example of a hemostatic device.

FIG. 3 depicts another example of an embodiment of a hemostatic device 310. In this example, a vessel and/or a dispensing component can comprise a syringe 320. In some embodiments, the vessel and/or dispensing component can be in fluid communication with a spray-producing component 340. In some embodiments, the dispensing component is a spray-producing component 340. The spray-producing component 340 may be capable of dispensing the hemostatic composition in a form comprising a spray. The syringe 320 may further comprise a reservoir cylinder 350 which may contain a liquid hemostatic composition 330 and which may be in fluid communication with the spray producing component 340. A plunger 360 may be slidably disposed within the reservoir cylinder 350. A user may apply force to the plunger 360 in the direction 370 of the spray producing component 340 so as to apply pressure to the liquid hemostatic composition 330 in the reservoir cylinder 350, thus, forcing the liquid hemostatic composition 330 through the spray producing component 340 to produce a spray of the liquid hemostatic composition 330.

Figure 4:
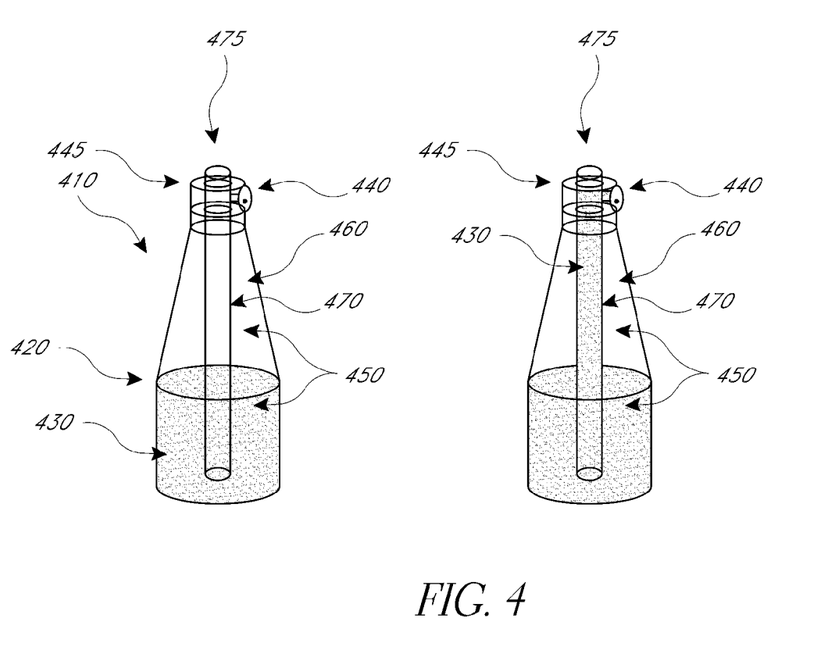
FIG. 4 depicts another schematic example of a hemostatic device.
Figure 5:
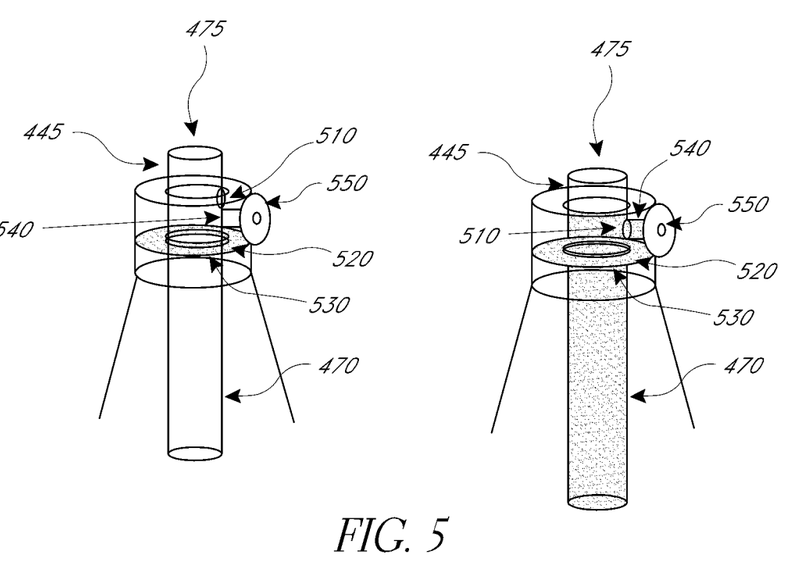
FIG. 5 is an expanded view of a portion of the example of a hemostatic device of FIG. 4.

FIGS. 4-5 depicts another example of an embodiment of a hemostatic device 410. In this example, the dispensing component may comprise a foam or spray producing component (referred to hereinafter as "spray component") 440. The spray component 440 may be capable of dispensing the hemostatic composition in a form comprising a foam or spray. The device may further comprise a propellant gas 450, which may fill the headspace 460 above the liquid hemostatic composition 430 and be dissolved in the liquid 430 so that when the spray component 440 is opened, the pressure difference may cause foam or spray to be dispensed. The propellant gas dissolved in the liquid may provide foam or spray as the dissolved gas expands under the reduced pressure. Inert gases, such as nitrogen, carbon dioxide, and fluorocarbons, may be useful as propellants.

As shown in FIG. 4, the spray component 440 may comprise a closed tube 470, which may be closed at the top 475 and partially submerged below the surface of the liquid hemostatic composition 430. The spray component may further comprise a cap 445, which may be movably connected to the tube 470.

FIG. 5 depicts an expanded view of parts of the spray component 440 which may allow the spray component to be opened so that the liquid hemostatic composition 430 may be dispensed. The tube 470 may comprise an orifice 510, and may be movably connected to a bottom platform 530 of the cap 445. The tube 470 may be further coupled to a spring 520 which may abut and may be supported by the bottom platform 530 of the cap 445. When the spring 520 and tube 470 are in a relaxed position, the orifice 510 may be located just above a channel 540 in the cap 445. The channel may be in fluid communication with an exit port 550, which may be in fluid communication with the outside of the device. When a user pushes the tube 470 downward, the orifice 510 may become coupled to the channel 540 to open fluid communication between the tube 470 and the channel 540 so that the pressure from the propellant gas may force the liquid hemostatic composition 430 out of the exit port 550. When the liquid hemostatic composition 430 has been dispensed, the user may release the force on the tube 470 so that the spring 520 may return the tube 470 to the relaxed position.

A hemostatic composition may be incorporated into other systems or methods in many different types of various applications, such as surgery. These methods or systems may comprise a hemostatic composition in liquid form (or a "hemostatic liquid") and a liquid provision component configured to provide the hemostatic liquid to an area of a human being or animal affected by a surgical procedure, such as an area that is bleeding as a result of a surgical procedure. The liquid provision component may be any structure, component, or device which is capable of providing the hemostatic liquid to the area affected by a surgical procedure (e.g., through irrigation). For example, the hemostatic liquid may be provided during surgery, while surgery is being completed, after surgery is completed, etc. Examples may include, but are not limited to, surgical tubing with a hand piece comprising a valved dispensing portion to permit selective dispensing or irrigation. A system or method may further comprise a liquid-removal component configured to remove liquids, such as the hemostatic liquid, blood, or other liquids, from the area of the human being or animal affected by the surgical procedure (e.g., through aspiration). The liquid-removal component may be any structure, component, or device which is capable of removing liquid from the area affected by a surgical procedure. Examples may include, but are not limited to, tubing, such as surgical tubing. The liquid removal component may further be configured to remove the hemostatic liquid while the surgery is taking place, as surgery is being completed, after surgery is completed, etc. The liquid-delivery and liquid-removal components can be included together on a single hand piece or can be provided separately. An actuator positioned on the hand piece or surgical tubing can activate either or both of the irrigation and aspiration features, or toggle between them.

Figure 6A:
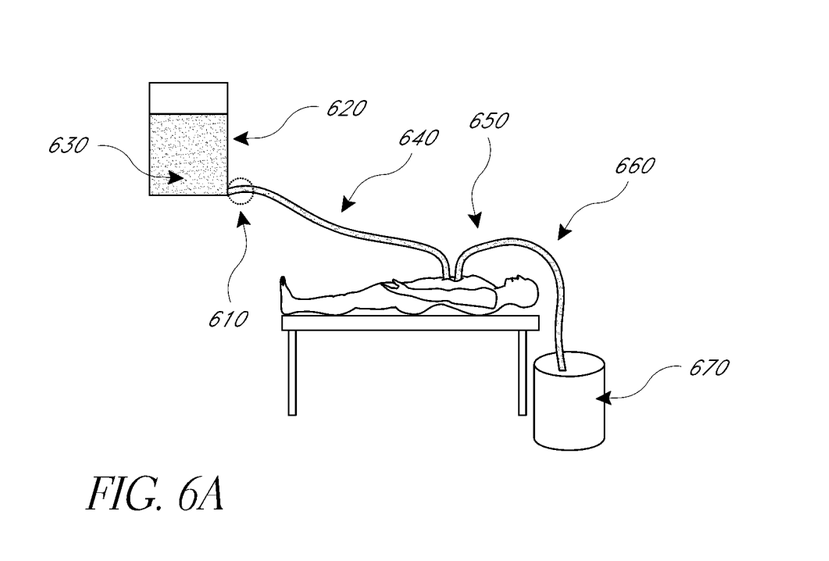
FIG. 6A depicts an example of a system which may be used in applications such as surgery.

FIG. 6A is a schematic of an example of a system which may be used in applications such as surgery. In this example, a vessel 620 may be in fluid communication with an optional pump 610. The pump 610 may in turn be in fluid communication with a first surgical tube 640, so that the pump 610 delivers the liquid hemostatic composition 630 through the first surgical tube 640 to provide hemostasis at the wound site and to deliver a hemostatic composition to a patient 650 who is undergoing surgery. In this example, a second surgical tube 660 may also be provided through which spent liquid hemostatic composition and other liquids may be released into a waste receptacle 670. In some circumstances, the pump may be omitted and circulation of the liquid hemostatic composition may be accomplished by other means. For example, the vessel 620 may be placed in a higher vertical position than the patient 650, and the waste receptacle 670 may be placed in a lower vertical position than the patient so that gravity drives the circulation.

Figure 6B:
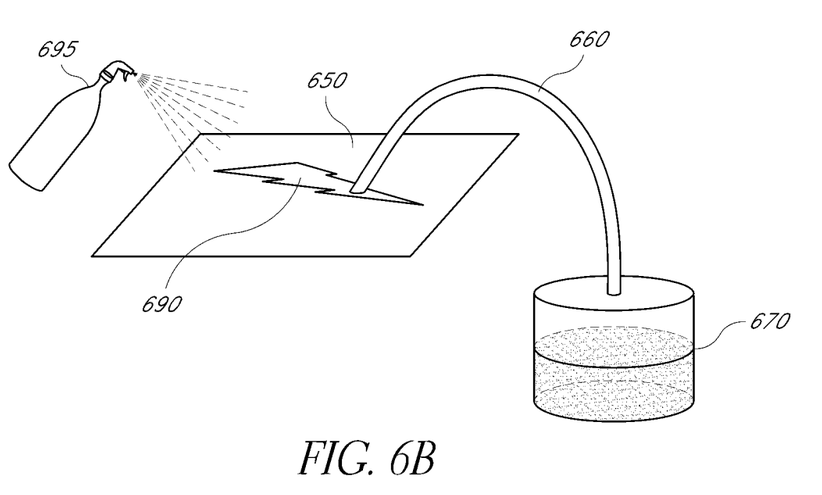
FIG. 6B depicts another example of a system which may be used in applications such as surgery.

FIG. 6B is a schematic of another example of a system which may be used in applications such as surgery. In this example, a vessel 695 may comprise a foam or spray producing component similar to spray component 440 illustrated in FIGS. 4-5. Vessel 695 may be used to manually or periodically deliver a liquid spray or foam of the hemostatic composition to a wound or opening 690 in a patient 650 who is undergoing surgery. In this example, a second surgical tube 660 may also be provided through which spent liquid hemostatic composition and other liquids may be released into a waste receptacle 670. In some circumstances, the waste receptacle 670 may be placed in a lower vertical position than the patient so that gravity drives the circulation. Alternatively, suction may be applied through tube 660 to remove spent liquid hemostatic composition.

In some embodiments, a hemostatic system may comprise a hemostatic device that may comprise a vessel and a hemostatic composition. The vessel may be any vessel which is configured to contain a liquid. This vessel may further comprise an interior volume configured to contain a liquid, and an orifice in fluid communication with the interior volume comprising a rim surrounding the orifice, wherein the rim is configured to generally provide contact with or to generally form a seal with a part of an animal body or a human body.

A rim may be a rim similar to a rim of a cup or a glass, or it may simply be formed by a hole on an external surface of the vessel. It may be even with an external surface of the vessel or may be raised with respect to the surface of the vessel. In some embodiments, the rim may be flexible or resilient. A seal may be formed by causing the rim to be pressed against the body part and/or by disposing an adhesive material on the rim so that a seal is formed by temporary adhesion between the rim and the body part.

A vessel may further comprise a fluid input component configured to provide a liquid to an interior volume of the vessel. The fluid input component may be any structural feature or combination of features which may provide a liquid to an interior volume of a vessel, such as an orifice or a valve.

A vessel may further comprise a fluid output component configured to allow liquid to exit from the vessel. The fluid output component may be any structural feature or combination of features which may allow liquid to exit from the vessel, such as an orifice or a valve.

Figure 7:
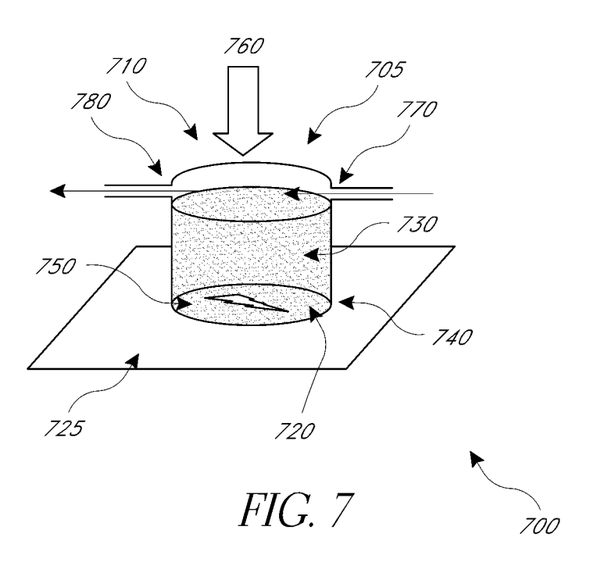
FIG. 7 depicts an example of a hemostatic device.

FIG. 7 depicts an example of a hemostatic device 700 that may be applied to a bleeding area, open wound, or a surgical opening in the body. This example may have an inverted vessel 705 having a closed top 710 and an open bottom 720 having a rim 740. The bottom 720 may be placed on a surface 725 of an injured person or patient so that the rim 740 is generally proximate to and/or generally surrounds the injury or opening 750. Pressure 760 may be applied to the device so that the rim 740 and the surface 725 form a seal that generally obstructs or prevents liquid from escaping. In some embodiments, an adhesive material (not shown) may be disposed on the rim 740 so that a seal is formed between the rim 740 and the surface 725. A hemostatic composition 730 may be circulated by an inlet 770 through which the hemostatic composition 730 may enter the device and an outlet 780 through which the hemostatic composition 730 and other fluid may exit the device 700.

Example 1

Kaolin (about 0.34 g) and glycerin (about 0.91 g) are mixed with sterile, distilled, non pyrogenic, pH 7.0 water (about 42 mL). The mixture appears cloudy or turbid.

Example 2

The mixture of Example 1 is centrifuged for about 5 minutes at about 3000 rpm. The supernatant is carefully collected and the precipitate is discarded to yield a liquid hemostatic composition which appears substantially clearer.

Example 3

The composition of Example 2 (about 3 mL) is combined with 10% povidone iodine (about 3 mL).

Example 4

The composition of Example 2 (about 6 mL) is combined with 10% povidone iodine (about 3 mL).

Example 5

The compositions prepared as described in Examples 1-3, and water were tested for clotting. The test was carried out by combining 0.5 ml of the hemostatic composition with 1 ml of citrated sheep blood and 150 µL of $CaCl_2$ in a test tube.

The clotting times for the four samples are shown in Table 1 below.

TABLE 1

| Composition | Clotting Time (Min:Sec) |
| --- | --- |
| Example 1 | 1:30 |
| Example 2 | 1:45 |
| Example 3 | 2:45 |
| Example 4 | 2:30 |
| Water | 6:30 |

Although the embodiments have been described in the context of certain examples, it will be understood by those skilled in the art that the scope of the claims may extend beyond the specifically disclosed embodiments to other embodiments including embodiments formed of combinations of features disclosed herein and equivalents thereof.

The following is claimed:

1. A hemostatic device comprising:
   an absorbent material;
   a composition comprising a clay hemostatic agent and hydroxypropylmethylcellulose;
   wherein the clay hemostatic agent is kaolin;
   wherein the composition is suspended in a liquid to form a suspension;
   wherein the suspension is absorbed onto the absorbent material during preparation of the hemostatic device; and wherein the clay hemostatic agent comprises about 10% or less of the weight of the suspension.

2. The hemostatic device of claim 1, wherein the absorbent material is selected from the group consisting of a sponge, a cloth, and a gauze.

3. The hemostatic device of claim 1, wherein the hemostatic device further comprises one or more of bentonite, montmorillonite, saponite, polygorskite or attapulgite, and sepiolite.

4. A hemostatic device comprising:
an absorbent material;
a composition comprising a clay hemostatic agent and a thickening agent selected from the group consisting of hydroxypropylmethylcellulose, methylcellulose, and hydroxypropylcellulose;
wherein the clay hemostatic agent is kaolin; and
wherein the composition is suspended in a liquid and absorbed onto the absorbent material during preparation of the hemostatic device.

5. The hemostatic device of claim 4, wherein the absorbent material is selected from the group consisting of a sponge, a cloth, and a gauze.

6. The hemostatic device of claim 4, wherein the hemostatic device further comprises one or more of bentonite, montmorillonite, saponite, polygorskite or attapulgite, and sepiolite.

7. The hemostatic device of claim 4, wherein the thickening agent is a gelling agent.

8. The hemostatic device of claim 4, wherein the thickening agent is hydroxypropylmethylcellulose.

9. A hemostatic device configured to halt the flow of blood from a bleeding wound, the hemostatic device comprising:
an absorbent gauze;
a hemostatic clay applied to the gauze such that the clay is configured to be dispensed onto a bleeding wound when the hemostatic device is applied to the bleeding wound;
a composition comprising hydroxypropylmethylcellulose applied to the gauze;
wherein the hemostatic clay comprises kaolin; and
wherein the gauze is not saturated with liquid such that the gauze is capable of absorbing blood when the hemostatic device is applied to a bleeding wound.

10. The hemostatic device of claim 9, wherein the hemostatic device is dry.

11. The hemostatic device of claim 9, wherein the hemostatic device is provided in a sterilized package.

12. The hemostatic device of claim 9, wherein the hydroxypropylmethylcellulose acts as a thickening agent.

* * * * *

UNITED STATES PATENT AND TRADEMARK OFFICE
CERTIFICATE OF CORRECTION

PATENT NO. : 9,889,154 B2
APPLICATION NO. : 14/995592
DATED : February 13, 2018
INVENTOR(S) : Basadonna et al.

It is certified that error appears in the above-identified patent and that said Letters Patent is hereby corrected as shown below:

On the Title Page

In Column 2 (page 6, item (56)) at Line 1, Under Other Publications, change "NATO/OTAM," to --NATO/OTAN,--.

In the Specification

In Column 3 at Line 45, Change "polygorskite" to --palygorskite--.

In Column 4 at Line 24, After "etc.)" insert --,--.

In Column 4 at Line 47, Change "Turbitidy" to --Turbidity--.

In Column 5 at Line 45, Change "chloropheniramine" to --chlorpheniramine--.

In Column 6 at Line 32, Change "etc.) magnesium" to --etc.), magnesium--.

In the Claims

In Column 11 at Line 8, In Claim 3, change "polygorskite" to --palygorskite--.

In Column 11 at Line 25 (approx.), In Claim 6, change "polygorskite" to --palygorskite--.

Signed and Sealed this
Third Day of July, 2018

Andrei Iancu
*Director of the United States Patent and Trademark Office*